(12) United States Patent
Thomas

(10) Patent No.: US 8,747,773 B2
(45) Date of Patent: Jun. 10, 2014

(54) PORTABLE DETECTION APPARATUS FOR BEVERAGE INGREDIENTS

(76) Inventor: Maryse Thomas, Victoria, MN (US)

(*) Notice: Subject to any disclaimer, the term of this patent is extended or adjusted under 35 U.S.C. 154(b) by 0 days.

(21) Appl. No.: 13/207,933

(22) Filed: Aug. 11, 2011

(65) Prior Publication Data

US 2011/0293799 A1 Dec. 1, 2011

Related U.S. Application Data

(63) Continuation of application No. 12/480,127, filed on Jun. 8, 2009.

(60) Provisional application No. 61/059,565, filed on Jun. 6, 2008.

(51) Int. Cl.
*G01N 21/75* (2006.01)

(52) U.S. Cl.
USPC ........... 422/400; 422/401; 422/420; 422/421; 422/423; 422/425; 422/426; 422/427; 422/428; 422/429; 422/68.1; 422/82.05; 422/82.06; 436/164; 436/169; 436/170; 435/13; 435/283.1; 435/287.1; 435/287.7; 435/287.8; 435/287.9; 435/288.7

(58) Field of Classification Search
USPC ......... 422/400, 401, 420, 421, 422, 423, 424, 422/425, 426, 427, 428, 429, 68.1, 82.05, 422/82.06; 436/164, 169, 170; 435/283.1, 435/287.1, 287.7, 287.8, 287.9, 288.7
See application file for complete search history.

(56) References Cited

U.S. PATENT DOCUMENTS

| | | | |
|---|---|---|---|
| 5,610,072 A | 3/1997 | Scherl et al. | |
| 5,817,454 A | 10/1998 | Harris et al. | |
| 5,824,554 A | 10/1998 | McKay | |
| 6,153,147 A | 11/2000 | Craig | |
| 6,461,873 B1 | 10/2002 | Catania et al. | |
| 6,500,665 B2 | 12/2002 | Deegan | |
| 6,703,216 B2 * | 3/2004 | Parsons et al. | 435/25 |
| 2001/0009758 A1 | 7/2001 | Harris et al. | |
| 2001/0046710 A1 * | 11/2001 | Cutler | 436/24 |
| 2002/0132358 A1 | 9/2002 | Deegan | |
| 2003/0111003 A1 * | 6/2003 | Engelman et al. | 116/206 |
| 2004/0121420 A1 * | 6/2004 | Smith | 435/18 |
| 2005/0079629 A1 * | 4/2005 | Guo et al. | 436/169 |
| 2008/0095912 A1 | 4/2008 | Loughran | |
| 2009/0286322 A1 * | 11/2009 | Dancer | 436/20 |
| 2010/0035332 A1 | 2/2010 | Thomas | |

FOREIGN PATENT DOCUMENTS

| | | | | |
|---|---|---|---|---|
| WO | WO 2005059541 A1 * | 6/2005 | | G01N 33/14 |
| WO | WO 2006079167 A1 * | 8/2006 | | |

OTHER PUBLICATIONS

"U.S. Appl. No. 12/480,127 Non-Final Office Action mailed Oct. 6, 2010", 4 pgs.
"U.S. Appl. No. 12/480,127, Supplemental Final Office Action mailed May 11, 2011", 12 pgs.
"U.S. Appl. No. 12/480,127, Final Office Action mailed Mar. 11, 2011", 9 pgs.
"U.S. Appl. No. 12/480,127, Response filed Feb. 7, 2011 to Non Final Office Action mailed Oct. 6, 2010", 8 pgs.

* cited by examiner

*Primary Examiner* — Dennis M White
(74) *Attorney, Agent, or Firm* — Schwegman Lundberg & Woessner, P.A.

(57) ABSTRACT

Embodiments of the invention relate to portable detection apparatus, comprising one or more detector regions adapted to visually indicate the presence or amount of an analyte in a beverage. The detection apparatus is shaped substantially the same as a consumer product.

19 Claims, 1 Drawing Sheet

PORTABLE DETECTION APPARATUS FOR BEVERAGE INGREDIENTS

CROSS REFERENCE TO RELATED APPLICATION(S)

This present application is a continuation and claims the benefit of priority under 35 U.S.C. §120 to U.S. patent application Ser. No. 12/480,127, filed on Jun. 8, 2009, which claims the benefit under 35 U.S.C. §119(e) of U.S. Provisional Patent Application Ser. No. 61/059,565 filed Jun. 6, 2008, the contents of which are hereby incorporated herein by reference in its entirety.

BACKGROUND

The detection of various ingredients in beverages is desirable for a number of reasons, but most importantly for health and safety. Some beverages advertised as non-caffeinated or sugar-free may actually contain those substances. In addition, the placement of illicit drugs in beverages is on the rise.

Most detection methods of such substances are straightforward in a laboratory setting. But the detection methods have not been successfully carried over to portable devices for use in a social setting. For those devices or apparatus that do exist, they are often bulky and easily identifiable. This leads to a reluctance of the user to utilize the apparatus in public.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

SUMMARY

Embodiments of the invention relate to portable detection apparatus, comprising one or more detector regions adapted to visually indicate the presence or amount of an analyte in a beverage. The detection apparatus is shaped substantially the same as a consumer product.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

Embodiments of the invention relate to a portable detection apparatus for use with beverages. The apparatus may be shaped as to be easily portable and also inconspicuous in a social setting. The apparatus may be shaped as various small, consumer items, such as match books, makeup compacts, straws, stirrers, etc. The apparatus may be able to detect one or more ingredients in a beverage. The apparatus may detect whether a drink contains caffeine and may be able to identify how much caffeine is present. The apparatus may detect the presence and amount of sugar, which may be very valuable to diabetics. For public safety reasons, it may be desirable to test for the presence of illicit drugs. Examples of illicit drugs that may be detectable include GHB (gamma hydroxybutryate), ketamine, Rohypnol® (flunitrazepam), methadone, opiates, marijuana, amphetamines, cocaine, benzodiazepines and their metabolites and ecstasy (MDMA). The apparatus may also be utilized to detect bacteria and other beverage contaminants.

Figure 1:
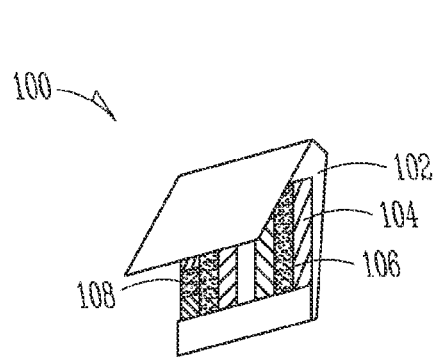
FIG. 1 illustrates a perspective view of a portable detection apparatus with detection strips, according to some embodiments.

Referring to FIG. 1, a perspective view 100 of a portable detection apparatus with detection strips is shown, according to some embodiments. A match book shaped apparatus 102 may include one or more analyte detection strips 104 or regions on a strip. Each strip may detect one or more analytes when contacted with a beverage sample. For example, the strip 104 may detect caffeine, another strip 106 may detect sugar content and a third strip 108 may detect three types of illicit drugs.

Caffeine may be one substance detected. The detector region or strips 104 may be impregnated with a reagent that changes color when reacted with caffeine. The degree of color change may then be proportional to the concentration of caffeine in the beverage. The apparatus may be provided with a graded color chart which can be compared to the color of the strip 104 so as to ascertain the concentration of caffeine in the beverage. The strip or detector region may include a beverage dipping section; an adjacent temperature moderation section; and an adjacent reagent-impregnated section. The beverage may be wicked from its container to the reagent-impregnated section of the strip. In this manner, the reagent may never directly admix with the beverage in the container.

Caffeine may be detected by utilizing a xanthine oxidase enzyme reaction to produce a chromogenic change on the detector region. The reagent section of the region may contain xanthine oxidase enzyme coupled with a horseradish peroxidase enzyme; a buffer (pH 7.5 phosphate buffer); and a chromogen which produces a color change on the detector region when a coupled enzymatic reaction takes place. The xanthine oxidase may be immobilized by cross linking with a reagent such as glutaraldehyde on a surface which may be coated with a material such as gelatin, polyacrylamide, alginates, or the like. The reaction of $O_2$ and caffeine in the presence of the xanthine oxidase enzyme produces hydrogen peroxide ($H_2O_2$) and oxidized caffeine. The $H_2O_2$ formed reacts with the chromogen in the presence of the peroxidase enzyme to produce an oxidized form of the chromogen whose hue varies with the concentration of hydrogen peroxide, and thus caffeine. The calibration strip, or a separate calibration chart, with fixed colors for different concentration ranges may be compared with the color produced by the beverage of unknown caffeine content in order to complete the analysis.

Another example may utilize an apoenzyme reactivation reaction to produce a chromogenic change in the region area. The reagent section of the strip or region may contain monoclonal antibodies reactive against caffeine; a caffeine conjugate labeled with flavin adenine dinucleotide (FAD); apoglucose oxidase which reacts with unbound caffeine conjugate; a chromogen buffer; and peroxidase. Competitive binding between caffeine and caffeine conjugate on the antibody releases more conjugate for reaction with the apoglucose enzyme thereby increasing the amount of hydrogen peroxide produced by the glucose oxidase reaction. The chromogen color will vary in hue depending on the concentration of hydrogen peroxide, and thus on caffeine concentration. Again, a calibration chart with fixed colors may be used to complete the quantitative assay. In both methods described above, chromogens which could be used include potassium iodide (KI) chromogen, tetramethylbenzidine, and homovanillic acid.

Another method of detection may include a first region including phosphodiesterase enzyme, a second region including cyclic AMP, and a means for indicating inhibition of degradation of the cyclic AMP by the phosphodiesterase due to the presence of caffeine or the like. The method includes contacting a portion of the beverage with a phosphodiesterase enzyme and cyclic AMP, and further contacting the portion with the means for indicating the inhibition, typically a pH indicator paper.

The caffeine may also be detected by using a molecular imprint polymer (MIP) as a chromatographic medium. A "molecular imprint polymer" is a polymer which is prepared by polymerizing monomers around a template or "print" molecule, which is then removed from the polymer by extraction or other means so that the polymer will selectively absorb the template or print molecule upon re-exposure to the print molecule. U.S. Pat. Nos. 5,821,311, 5,872,198, and 5,959,050, issued Oct. 13, 1998, Feb. 16, 1999, and Sep. 28, 1999, respectively, to Mosbach, et al. describe certain MIP polymers, a polymerization process, and symmetrical beads produced by suspension polymerization from functional monomers for use as chromatographic media. U.S. Pat. No. 5,814,223 and 5,916,445, issued Sep. 29, 1998 and Jun. 29, 1999, respectively, to Hjerten, et al., disclose a gel type chromatographic media and method for preparing the media, the media being formed by a molecular imprint polymer prepared from a nonionizable polymerizable substance which is nonreactive to the imprinted molecule.

Further examples of caffeine detection are shown in U.S. Pat. Nos. 5,610,072; 5,817,454; 5,824,554; 6,461,873; 6,500,665; U.S. Pat. App. No. 2008/0095912; U.S. Pat. App. No. 2002/0132358; and U.S. Pat. App. No. 2001/0009758, the disclosures of which are herein incorporated by reference.

To detect sugars, a detection region may be impregnated with the enzymes glucose oxidase (Aspergillus Niger) and peroxidase (horseradish), and a color indicator. When a sugary beverage reaches the indicator section, the glucose may be oxidized to gluconic acid and hydrogen peroxide, with glucose oxidase acting as a catalyst. The hydrogen perxide oxidizes an oxygen acceptor to provide visible color change. Alternatively, the detector region may be impregnated with glucose oxidase, peroxidase, o-Tolidine, 3-Amino-9-(y-aminopropyle)-carbazole-dihydrochloride, buffer, and non-reactive ingredients. When a sugary beverage reaches the indicator section, the reaction previously described takes place. Examples of sugar detection may be found in U.S. Pat. App. 2003/0111003.

Illicit drugs may be detected in a number of ways. A beverage sample suspected of containing GHB may be contacted with a first oxidoreductase selective for GHB and an oxidized cofactor. In the presence of GHB in the sample, the first oxidoreductase oxidizes GHB to succinic semialdehyde and reduces the cofactor. The reduced cofactor thus produced can be detected directly, or a hydride abstractor can be used that abstracts a hydride from the reduced cofactor and produces a detectable change. The hydride abstractor can be a second oxidoreductase that oxidizes the reduced cofactor and produces a detectable change in a chromogen or dye. A visual change may then be produced, allowing performance of the assay outside of a laboratory setting. Examples of detection of GHB and other illicit drugs are found in U.S. Pat. Nos. 6,703,216; 7,238,533, U.S. Pat. App. No. 2008/0102483; U.S. Pat. App. No. 2003/0044989; U.S. Pat. App. No. 2001/0046710, the disclosures of which are herein incorporated by reference.

Figure 2:
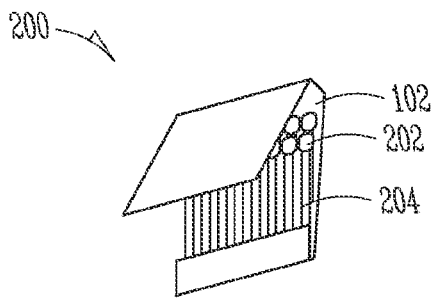
FIG. 2 illustrates a perspective view of a portable detection apparatus with match-shaped detection probes, according to some embodiments.

Referring to FIG. 2, a perspective view 200 of a portable detection apparatus with match-shaped detection probes is shown, according to some embodiments. A match book shaped apparatus 102 may include one or more analyte detection probes 204 shaped or disguised as matches. The detection chemicals may be positioned in the head 202 of the match, in the body of the match or in both, for example.

Figure 3:
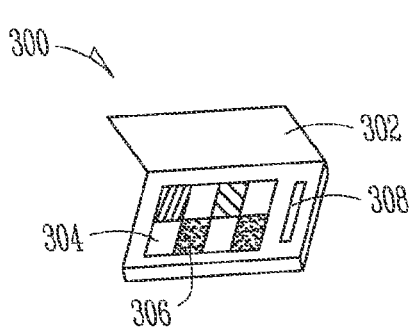
FIG. 3 illustrates a perspective view of a portable detection apparatus shaped as a consumer's makeup compact, according to some embodiments.
Figure 4:
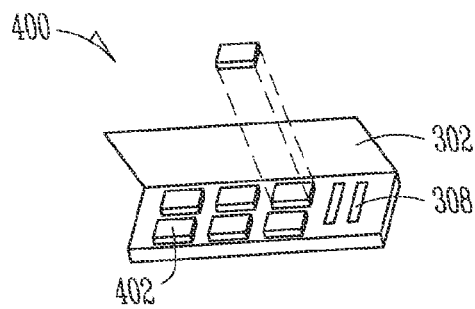
FIG. 4 illustrates a perspective view of a portable detection apparatus utilizing removable detection units, according to some embodiments.
Figure 5:
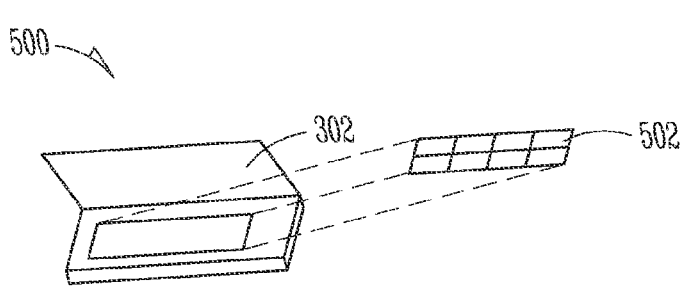
FIG. 5 illustrates a perspective view of a portable detection apparatus utilizing a removable detection cartridge, according to some embodiments.

Referring to FIG. 3, a perspective view 300 of a portable detection apparatus shaped as a consumer's makeup compact is shown, according to some embodiments. A detection apparatus may be shaped to various configurations that are easy to carry and are inconspicuous. The apparatus may be a compact shaped apparatus 302. The compact detector 302 may include one or more detection regions 304, 306 and an applicator 308. The optional applicator 308 may be used to apply a sample of a beverage to the detection regions. The detector regions may be individual detection units 402 (see view 400 in FIG. 4) that are removable or replaceable. The units 402 may be disposable or cleaned and re-used depending on the type of detection performed. The detector units or regions may make up a detector cartridge 502 (see view 500 in FIG. 5). The cartridge 502 may be removable or replaceable, for example.

Figure 6:
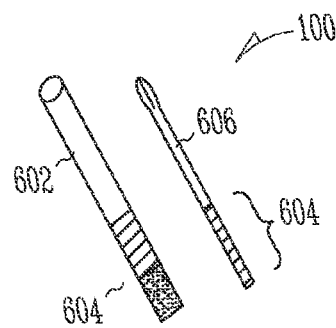
FIG. 6 illustrates a perspective view of a portable detection apparatus utilizing a stirrer or straw-shape, according to some embodiments.

Referring to FIG. 6, a perspective view 600 of a portable detection apparatus utilizing a stirrer or straw-shape is shown, according to some embodiments. The apparatus may be shaped as a straw 602 or swizzle stick (stirrer) 606. One or more detector regions 604 may be positioned so as to easily contact a beverage.

What is claimed is:

1. A method of determining the presence or amount of one or more ingredients in a beverage, comprising:
   contacting a representative sample of a beverage and one or more detector regions of a plurality of detector regions, wherein a single detector cartridge includes the plurality of detector regions, the detector cartridge positioned within a portable detection apparatus such that the contacting occurs while the detector cartridge is positioned within the portable detection apparatus, wherein said portable detection apparatus has a shape resembling a makeup compact, the detector cartridge has a shape resembling a makeup container, the portable detection apparatus including an applicator removably positioned within portable detection apparatus and configured to contact the representative sample with the one or more detector regions, the applicator having a shape resembling a makeup applicator;

wherein a first detector region of the plurality of detector regions is configured to detect a first ingredient and a second detector region of the plurality of detector regions is configured to detect a second ingredient different from the first visually reading the one or more detector regions; and determining the presence or amount of one or more ingredients in the beverage from the reading of the one or more detector regions.

2. The method of claim 1, wherein the plurality of detector regions comprise a reagent-impregnated section that changes color when reacted with the one or more ingredients in the beverage.

3. The method of claim 1, wherein making the determination of the presence of one or more ingredients comprises detecting the presence of bacteria, sugar, an illicit drug, or an illicit drug metabolite, wherein making the determination of the amount of one or more ingredients comprises comparing the at least one detector region to a graded color chart.

4. The method of claim 1, wherein making the determination of the presence of one or more ingredients comprises detecting the presence of bacteria, caffeine, sugar, an illicit drug, or an illicit drug metabolite.

5. The method of claim 1, wherein making the determination of the presence of one or more ingredients comprises detecting the presence of GHB (gamma hydroxybutryate), ketamine, flunitrazepam, methadone, opiates, marijuana, amphetamines, cocaine, benzodiazepines, ecstasy (MDMA), or a drug metabolite.

6. The method of claim 1, wherein making the determination of the presence of one or more ingredients comprises detecting the presence of bacteria, sugar, an illicit drug, or an illicit drug metabolite, wherein the one or more detector regions further comprise an enzyme and a polymer.

7. The method of claim 1, wherein the single detector cartridge including the plurality of detector regions removable or replaceable from the portable detection apparatus.

8. A method of determining the presence or amount of one or more ingredients in a beverage, comprising:

contacting a representative sample of a beverage and one or more detector regions of a plurality of individual detector regions positioned within a portable detection apparatus, the portable detection apparatus having a shape resembling a makeup compact, and having at least a first and second component, contacting the representative sample including:

removing a first component from the portable detection apparatus, wherein the first component is an applicator, the applicator characterized by having a shape resembling a makeup applicator;

contacting the beverage sample with said first component;

utilizing the first component to apply the beverage sample to a second component, the second component is a first detector region of the plurality of individual detector regions, wherein the first detector region is characterized by having a shape resembling a makeup container, and wherein the beverage sample is applied to the first detector region while the plurality of individual detector regions are positioned within the portable detection apparatus;

visually reading the first detector region; and determining the presence or amount of one or more ingredients in the beverage from the at least one detector region, wherein the first detector region can be replaced while at least a second detector regions remains within the portable detection apparatus.

9. The method of claim 8, wherein the portable detection apparatus further comprises a replaceable or reusable component wherein the at least one detector region of the portable detection apparatus is replaceable.

10. The method of claim 8, wherein the step of contacting the beverage with the said first component comprises contacting a temperature moderation section and an adjacent reagent-impregnated section with the beverage.

11. The method of claim 8, wherein the plurality of detector regions comprise a reagent-impregnated section that changes color when reacted with the one or more ingredients in the beverage.

12. The method of claim 8, wherein the step of determining the presence or amount of one or more ingredients other than caffeine comprises comparing at least one detector region to a graded color chart.

13. The method of claim 8, wherein visually detecting the presence or amount of the one or more ingredients in the beverage comprises detecting the presence of sugar.

14. The method of claim 8, wherein visually detecting the presence or amount of the one or more ingredients in the beverage comprises detecting the presence of methadone or amphetamines, and their metabolites.

15. The method of claim 8, wherein visually detecting the presence or amount of the one or more ingredients in the beverage comprises detecting the presence of bacteria.

16. The method of claim 8, comprising immersing a removed detector region in the beverage so that the beverage sample is wicked from its container to a reagent-impregnated section of the removed detector region such that the reagent does not directly admix with the beverage remaining in the container.

17. The method of claim 8, wherein the plurality of detector regions further comprise an enzyme and a polymer.

18. The method of claim 3, wherein the detection step comprises contacting the beverage sample with a first oxidoreductase and a second oxidoreductase; the first and second oxidoreductase producing a visually detectable change that allows performance of the assay outside of a laboratory setting.

19. The method of claim 8, wherein visually detecting the presence or amount of the one or more ingredients in the beverage comprises detecting the presence of a GHB (gamma hydroxybutryate) metabolite, a ketamine metabolite, a flunitrazepam metabolite, an opiate metabolite, a marijuana metabolite, a cocaine metabolite, a benzodiazepine metabolite or an ecstasy (MDMA) metabolite.

* * * * *

UNITED STATES PATENT AND TRADEMARK OFFICE
CERTIFICATE OF CORRECTION

PATENT NO. : 8,747,773 B2
APPLICATION NO. : 13/207933
DATED : June 10, 2014
INVENTOR(S) : Maryse Thomas It is certified that error appears in the above-identified patent and that said Letters Patent is hereby corrected as shown below:

In the Claims

In column 5, line 17, in Claim 1, delete "first" and insert --first;--, therefor Signed and Sealed this
Twenty-fifth Day of November, 2014

Michelle K. Lee
*Deputy Director of the United States Patent and Trademark Office*